US00PP32737P2

(12) United States Plant Patent
Hansen

(10) Patent No.: US PP32,737 P2
(45) Date of Patent: Jan. 5, 2021

(54) ***BRUNNERA* MACROPHYLLA PLANT NAMED 'QUEEN OF HEARTS'**

(50) Latin Name: ***Brunnera macrophylla* (Adams) I. M. Johnston**
Varietal Denomination: Queen of Hearts

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/602,168

(22) Filed: Aug. 20, 2019

(51) Int. Cl.
*A01H 5/12* (2018.01)
*A01H 6/00* (2018.01)

(52) U.S. Cl.
USPC ..... Plt./412

(58) Field of Classification Search
USPC ..... Plt./412
See application file for complete search history.

*Primary Examiner* — Susan McCormick Ewoldt

(57) ABSTRACT

The new and distinctive cultivar of *Brunnera* plant named 'Queen of Hearts' with very large leaves of dense silver with thin dark green around the veins. The numerous flowers are light blue on tall stems for about four weeks in the spring. The new plant has thick leaves and is tolerant of high temperatures.

1 Drawing Sheet

Botanical classification: *Brunnera macrophylla* (Adams) I. M. Johnston.
Variety denomination: 'Queen of Hearts'.

STATEMENT REGARDING PRIOR DISCLOSURES UNDER 37 CFR 1.77(B)(6)

The first public disclosure of the claimed plant was a private sale to Corso's Flower and Garden Center by Walters Gardens, Inc. on Sep. 4, 2018. The claimed plant was disclosed on Dec. 1, 2018 as a non-enabling photograph and brief description on a website operated by Walters Gardens, Inc., who obtained the plant and all information relating thereto, from the inventor. No plants of *Brunnera* 'Queen of Hearts' have been sold in this country or anywhere in the world, nor has any disclosure of the new plant been made, more than one year prior to the filing date of this application, and such sale or disclosure within one year was either derived directly or indirectly from the inventor.

BACKGROUND AND ORIGIN OF THE PLANT

*Brunnera macrophylla* is a hardy, herbaceous, sub-alpine perennial native to eastern Asia, western Caucasus and Mediterranean Europe. It has many common names, among them: Heartleaf *Brunnera*, Siberian Bugloss, and Perennial Forget-me-not.

The new and distinct *Brunnera macrophylla* 'Queen of Hearts', hereinafter also referred solely by the cultivar name 'Queen of Hearts' and "the new plant," is a new and unique seedling hybridized by the inventor on May 15, 2015 between 'Alexander's Great' U.S. Plant Pat. No. 25,789 times a proprietary, unnamed, selfed seedling of 'Diane's Gold'(not patented). The new plant passed initial evaluation in the fall of 2016 and was assigned the breeder code 15-9-30 through the remaining evaluation process until given a cultivar name. 'Queen of Hearts' has been asexually propagated by sterile tissue culture propagation of the shoot tips, at the same nursery in Zeeland, Mich. since fall of 2016.

The asexually produced plants are identical to the originally plant, and maintains those unique characteristics in subsequent generations.

BRIEF DESCRIPTION OF THE PLANT

*Brunnera macrophylla* 'Queen of Hearts' is distinct from all other Heartleaf *Brunnera* known to the inventor. 'Jack Frost' U.S. Plant Pat. No. 13,859 has similar coloration, but the amount of silver covering the leaf is less, the green surrounding the leaf veins is greater in comparison, and the foliage is smaller in size. 'Looking Glass' U.S. Plant Pat. No. 17,829 has similar amount of silver covering the leaf, but the size is smaller, the quality is lower and the plant is less heat tolerant. 'Sterling Silver' U.S. Plant Pat. No. 31,280 has smaller leaf blades and smaller habit. The female parent, 'Alexander's Great', has more green and less silver in the leaves, and the green color is lighter and the silver less dense (with more green showing underneath). 'Alexander's Great' has shorter flower stems with fewer flowers. The male parent has yellow green foliage without any silver covering between the veins. 'Sea Heart' U.S. Plant Pat. No. 24,684 has more green surrounding the veins and less silver between the veins than the new plant. 'Silver Heart' U.S. Plant Pat. No. 24,685 has smaller foliage. Copending 'Jack of Diamonds' has broader green surrounding the leaf veins and less silver between the veins on the leaf blades. 'Queen of Hearts' has thicker leaves than 'Alexander's Great' and 'Jack Frost'.

*Brunnera* 'Queen of Hearts' differs from all other Heartleaf *Brunnera* in the following repeatedly observed trait combination:

1. Large herbaceous plants of rounded, clumping mounds, winter-hardy, perennial habit;
2. Foliage without a stem, held up on stiff petioles;
3. Very large, heart-shaped leaf blades having mostly dense silver between the veins with narrow dark green surrounding the veins;
4. Numerous flowers on very tall stems;

5. Leaves are cordate with thick, non-floppy substance;
6. Plant is tolerant of high temperatures.

BRIEF DESCRIPTION OF THE DRAWINGS

The photographs of the new invention demonstrate the overall appearance, including the unique traits, of a two-year-old plant growing in a partially shaded trial garden in Zeeland, Mich. The colors are as accurate as reasonably possible with color reproductions. Variation in ambient light spectrum, source and direction may cause the appearance of slight variation in brightness, saturation and hue.

DETAILED DESCRIPTION OF THE PLANT

Figure 1:
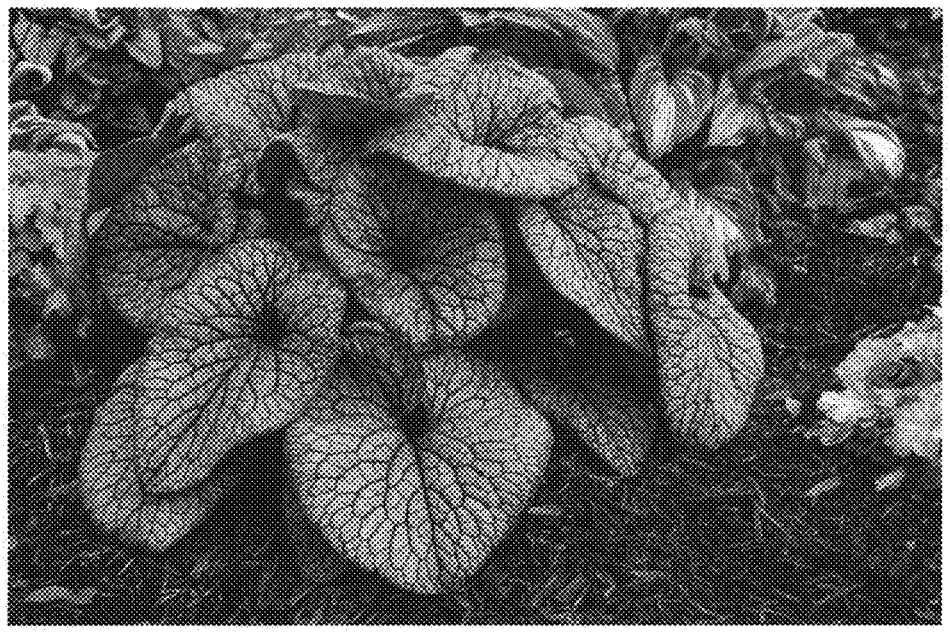
FIG. 1 shows a close-up of a leaf in early summer foliage.
Figure 2:
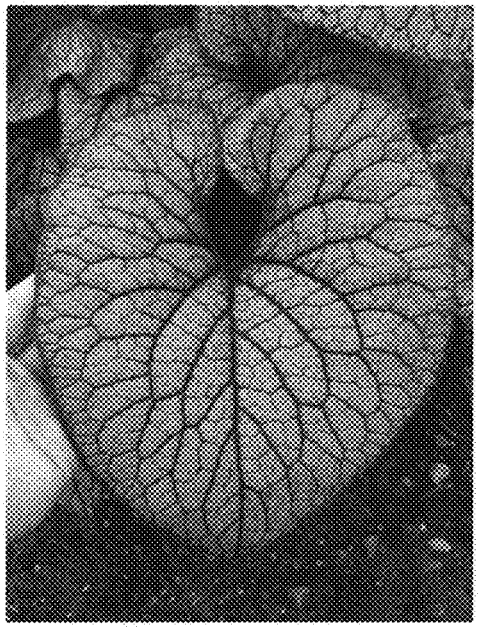
FIG. 2 shows the plant in the landscape in early summer foliage.
Figure 3:
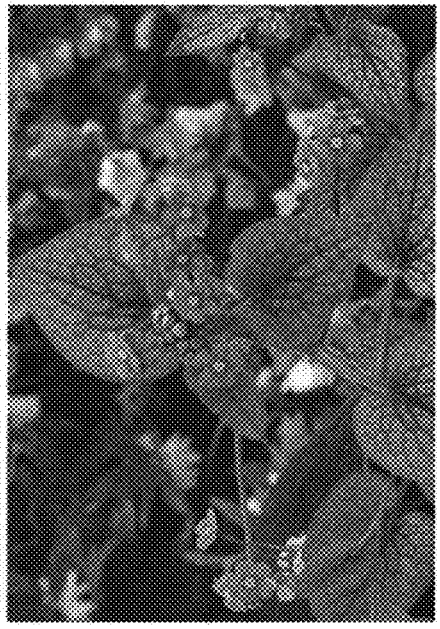
FIG. 3 shows a close-up of the flowers and buds.

The following descriptions with generic dictionary color usage are of a three-year-old plant growing in Zeeland, Mich. For more precise color descriptions the 2015 edition of The Royal Horticultural Colour Chart and the corresponding color references are used. The new plant has not been evaluated in all possible growing environments. The phenotype may vary slightly with different conditions such as fertility, light, moisture and temperature, however the genotype remains stable.

Plant habit: Winter-hardy, mounded, domed-shaped, herbaceous perennial of acaulescent foliage and with panicles in spring; foliage to 49.0 cm tall and 96.0 cm wide.

Leaves: Reniform to cordate; apex broadly acute; base cordate with lobes frequently imbricate; margin ciliolate; blade flat without undulations; adaxial and abaxial puberulent to hirsutulous; acaulescent leaves to about 29.0 cm long and about 28.0 cm in width, cauline leaves to about 5.5 cm wide and 6.0 cm long, decreasing distally; to about 14 acaulescent leaves per division, average about 6, 100 acaulescent leaves per clump about 5 cauline leaves per stem;

Leaf color: Acaulescent leaves — adaxial surface nearest RHS 137A to about 1.0 mm to 2.0 mm surrounding major veins and the margin 2.0 mm to 3.0 mm of leaf, silver portion between veins lighter than RHS 192D or RHS 190D; abaxial surface between RHS 146B and 146C; cauline leaves — in spring adaxial surface nearest RHS 138A along the marginal 2.0 mm to 3.0 mm and surrounding major veins and silver portion between veins between RHS 192A and RHS 190D;

Petioles: Pubescent, 14.0 mm wide and up to 32.0 cm long; distally nearest RHS 146C and proximally nearest RHS N77A;

Venation: Reticulate; impressed and glabrous adaxial, costate and hirsutulous abaxial;

Vein color: Adaxial main and secondary between RHS 161A and RHS 164B, abaxial nearest RHS 146D;

Inflorescence: Paniculate cyme with cauline leaves; to about 230 flowers; to about 99.0 cm tall and 6.5 mm diameter at base, flowering in distal 45.0 cm to about 24.0 cm wide;

Flower buds about one to two days prior to opening: Ellipsoidal; rounded apex and slightly attenuate base; to about 3.0 mm long and 2.0 mm diameter near apex;

Flower bud color: One day prior to opening — exposed petals nearest RHS 92D with petal margins intensified to nearest RHS 92B; sepals nearest RHS 143D; about three days prior to opening — exposed petals between RHS 75D and RHS 75D;

Flower lasting: Inflorescence remaining in effective flower for about four weeks, each flower persists up to one week;

Flower timing: Beginning late April and continuing for about four weeks;

Flower: Perfect; complete; actinomophic; rotate; forming five lobed corolla with center corona; about 7.0 mm diameter and corona eye about 2.0 mm tall and 1.5 mm across;

Petals: Typically five; rounded apex, truncate fused base; margin entire; to about 3.0 mm long and 2.0 mm wide;

Petal color: Adaxial mature face nearest RHS 104B with corona nearest RHS 158A, abaxial nearest 108 D; adaxial young face between RHS 104B and RHS 104A with corona nearest NN155D, abaxial nearest RHS 100C;

Sepals: Five; forming campanulate calyx; lanceolate; narrowly acute apex; fused in basal 0.7 mm; entire margin; about 1.5 mm long and about 0.5 mm across;

Sepal color: Nearest RHS 138B;

Peduncles: Cylindrical; pubescent to hirsutulous; erect; with cauline leaves; to about 99.0 cm and to 6.5 mm diameter;

Peduncle color: Distally nearest RHS 138B with undertone of nearest RHS 187A, proximally nearest RHS 187A;

Pedicels: Cylindrical; finely puberulent; mostly upright; to about 5.0 mm long and 1.0 mm diameter;

Pedicel color: Nearest RHS 138B with undertone of nearest RHS 187A;

Androecium: Five; fused to inner corona;

*Filaments.*—Cylindrical; about 1.0 mm long; color nearest RHS NN155D.

*Anther.*—Ellipsoidal: about 1.0 mm long and 0.5 mm diameter; basifixed; color nearest RHS 155A.

*Pollen.*—Nearest RHS 155A.

Gynoecium: One; about 1.2 mm long;

*Style.*—Short, cylindrical; about 0.5 mm long; color nearest RHS 145C.

*Stigma.*—Globose; about 0.2 mm diameter; color nearest RHS 145C.

Seeds: Small nutlet; enclosed within calyx; one to four per flower; about 0.5 mm diameter; color nearest RHS 202A;

'Queen of Hearts' is winter-hardy to USDA zone 3, tolerates late spring frosts, and persists after fall frosts. 'Queen of Hearts' performs best in light shade, with ample moisture, and good drainage. It is also well suited for growing in the landscape as a specimen plant, en mass, or in containers. 'Queen of Hearts' is less prone to leaf scorch than 'Variegata' (not patented) and is more tolerant of high temperatures than 'Looking Glass'. The new plant has shown no other susceptibility or tolerance to pests and diseases except that which is common to *Brunnera.*

I claim:

1. A new and distinct perennial Heartleaf *Brunnera* plant named 'Queen of Hearts' as herein described and illustrated.

* * * * *